United States Patent [19]

Kervin

[11] 4,329,984
[45] May 18, 1982

[54] ENDOTRACHEAL-TUBE STABILIZER

[76] Inventor: David Kervin, 61 Coachlight Ct., Springfield, Ill. 62703

[21] Appl. No.: 224,758

[22] Filed: Jan. 13, 1981

[51] Int. Cl.$^3$ ............................................ A61M 25/02
[52] U.S. Cl. ........................ 128/207.14; 128/DIG. 26
[58] Field of Search ................. 128/DIG. 26, 207.14, 128/207.15, 207.17, 12, 136, 133, 348, 349 R

[56] References Cited

U.S. PATENT DOCUMENTS

| | | | |
|---|---|---|---|
| 2,669,988 | 2/1954 | Carpenter | 128/136 |
| 2,882,893 | 4/1959 | Godfroy | 128/136 |
| 2,908,269 | 10/1959 | Cheng | 128/12 |
| 3,924,636 | 12/1975 | Addison | 128/DIG. 26 |
| 3,977,407 | 8/1976 | Coleman et al. | 128/DIG. 26 |

*Primary Examiner*—Henry J. Recla
*Attorney, Agent, or Firm*—Ralph F. Staubly

[57] ABSTRACT

To stabilize the inserted position of an endotracheal tube and to protect it against bite-damage, a bite-block of relatively rigid tough plastic has integrally connected front-edge flanges for overlying the upper and the lower lips of a patient for attachment thereto as by strips of adhesive tape, and has a forwardly extending vertically-on-edge flange for attachment thereto of the endotracheal tube as by adhesive tape wrapped therearound.

4 Claims, 4 Drawing Figures

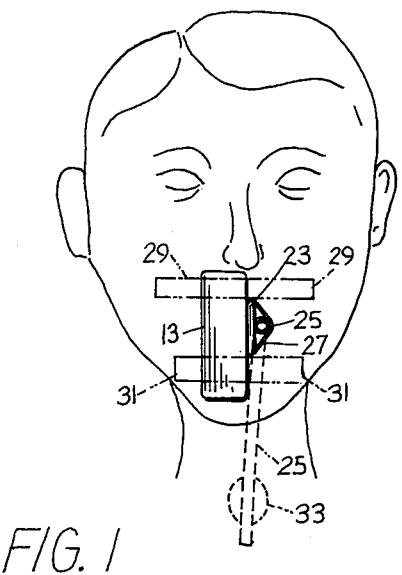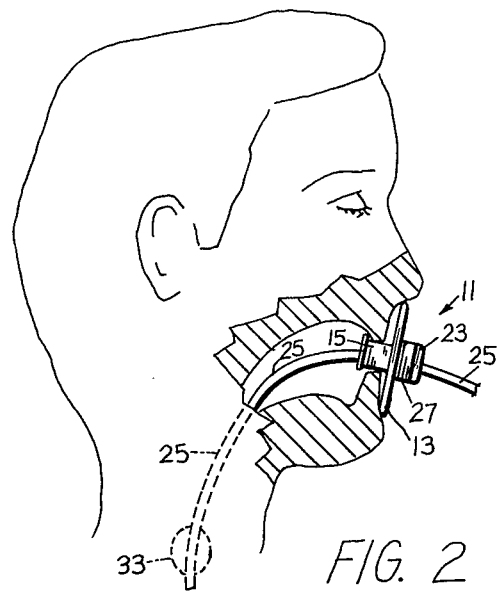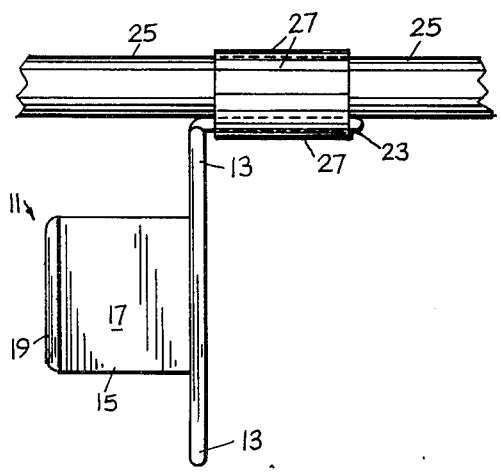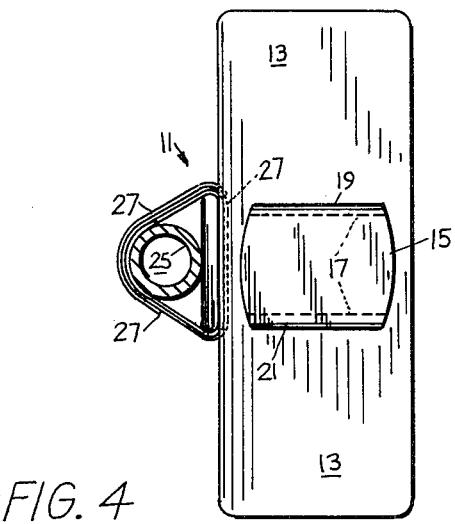

ENDOTRACHEAL-TUBE STABILIZER

BACKGROUND AND OBJECTS OF THE INVENTION

U.S. Pat. No. 1,498,810 to Poe discloses a complicated double-conduit "throat tube" surrounded by a "prop element" which element is designed to be placed between the upper and lower teeth of a patient to prevent damage to the throat tube by biting. It is the principal object of the present invention to provide a simple one-piece molded plastic body having a vertically extending mouth-bridging plate, a bite-block on the rear face of the plate and a forwardly extending side flange for attachment of an endotracheal tube thereto by adhesive tape. Other objects and advantages will become apparent as the following description proceeds.

BRIEF DESCRIPTIONS OF THE DRAWING FIGURES

FIG. 1 is a front elevational view of a preferred embodiment of the invention.

FIG. 2 is a left-side elevational partly-broken-away view of the showing of FIG. 1.

FIG. 3 is an enlarged plan view of the device of FIG. 2.

FIG. 4 is an enlarged rear elevational view of the disclosure of FIG. 2 (with the patient's head omitted).

DETAILED DESCRIPTION

With reference now to the drawings, the numeral 11 generally designates the endotracheal-tube stabilizer. The stabilizer 11 comprises a vertically disposable rigid mouth-spanning strap 13 onto which is integrally molded a bite-block 15 having flat top and bottom tooth-engagable surfaces 17. The surfaces 17 terminate at their rear edges in short and narrow upwardly and downwardly extending flanges 19 and 21, respectively, which retainingly engage behind the patient's teeth.

The stabilizer also has integrally molded thereon a forwardly extending vertically-on-edge flange 23 to which an endotraceal tube 25 can be easily and securely attached by wrapped-around adhesive-tape layers 27.

The stabilizer 11 is quickly, easily and securely held in place by two phantom-shown strips of adhesive tape 29 and 31 placed as shown in FIG. 1 and pressed against the face of the patient.

The stabilizer 11 may be plced either before or after the tube 25 is inserted (and has its retention below-larynx expansion balloon 33 inflated in known manner). When both the tube 25 and the stabilizer 11 are in place they are locked together by the wrap-around adhesive tape 27.

The invention having been described, what is claimed is:

1. An endotracheal-tube stabilizer, comprising: a first flange defining a front surface, a rear surface and opposing side edges, a bite block having a first end secured to the rear surface of said first flange and extending centrally in a substantially normal direction therefrom, said bite block having an upper and a lower surface adapted to be held in the mouth of a patient between the upper and lower teeth and being of a sufficient thickness to maintain the upper and lower teeth in spaced apart relation, said first flange having an upper portion extending laterally from said bit block in a substantially perpendicular direction to said upper bite surface and a lower portion extending laterally from said bit block in a substantially perpendicular direction to said lower bite surface, said upper and lower portions of said first flange being adapted to overlie the upper and lower lips of the patient, respectively, and be secured thereto as by strips of adhesive tape, a second flange secured to a side edge of said first flange and extending centrally therefrom in a direction substantially perpendicular to and outwardly from said front surface of said first flange, said second flange being adapted for attachment of an endotracheal tube thereto in a direction substantially perpendicular to said first flange as by wrapping adhesive tape therearound.

2. Structure according to claim 1, wherein said stabilizer is molded, in one piece, of a relatively rigid tough plastic material.

3. Structure according to claim 2 wherein said bite-block has an opposite second end including an upwardly and a downwardly extending retention flange extending from said upper and lower bite surfaces, respectively, adapted to be positioned behind the upper and the lower teeth, respectively, of a normal patient.

4. Structure according to claim 1 wherein said bite-block has an opposite second end including an upwardly and a downwardly extending retention flange extending from said upper and lower bite surfaces, respectively, adapted to be positioned behind the upper and the lower teeth, respectively, of a normal patient.

* * * * *